(12) United States Patent
Jeffrey

(10) Patent No.: US 7,670,313 B2
(45) Date of Patent: Mar. 2, 2010

(54) ACTUATOR AND CONTAINMENT DEVICE FOR A SYRINGE

(75) Inventor: Peter Jeffrey, Liverpool (GB)

(73) Assignee: Safe-T Limited, Isle of Man (GB)

( * ) Notice: Subject to any disclaimer, the term of this patent is extended or adjusted under 35 U.S.C. 154(b) by 751 days.

(21) Appl. No.: 10/566,181

(22) PCT Filed: Jul. 5, 2004

(86) PCT No.: PCT/GB2004/002921

§ 371 (c)(1),
(2), (4) Date: Jan. 27, 2006

(87) PCT Pub. No.: WO2005/014088

PCT Pub. Date: Feb. 17, 2005

(65) Prior Publication Data

US 2006/0253073 A1  Nov. 9, 2006

(30) Foreign Application Priority Data

Jul. 30, 2003 (GB) .................. 0317800.1

(51) Int. Cl.
*A61M 5/00* (2006.01)
(52) U.S. Cl. .................................... 604/110
(58) Field of Classification Search ........ 604/110, 604/197, 198
See application file for complete search history.

(56) References Cited

U.S. PATENT DOCUMENTS

| 5,211,628 | A | 5/1993 | Marshall |
| 5,324,265 | A | 6/1994 | Murray et al. |
| 5,330,430 | A | 7/1994 | Sullivan |
| 5,458,576 | A | 10/1995 | Haber et al. |
| 5,487,732 | A | 1/1996 | Jeffrey |
| 5,957,897 | A | 9/1999 | Jeffrey |
| 6,585,702 | B1 | 7/2003 | Brunel |
| 2003/0065290 | A1 * | 4/2003 | Shyu .................. 604/187 |

FOREIGN PATENT DOCUMENTS

| EP | 0272035 | 6/1988 |
| EP | 0636381 | 2/1995 |
| EP | 0747075 | 12/1996 |
| FR | 2650187 | 2/1991 |
| GB | 2341804 | 3/2000 |

(Continued)

*Primary Examiner*—Nicholas D Lucchesi
*Assistant Examiner*—Victoria P Campbell
(74) *Attorney, Agent, or Firm*—Dennison, Schultz & MacDonald

(57) ABSTRACT

To eliminate needle-stick risk by encapsulating the needle of a syringe immediately after discharge of syringe contents, the entire syringe is housed in a device comprising a hollow body, a spring and a plunger. The barrel of the syringe is held in the body interior against the force of the spring by latching formations internal to the body. The plunger is hollow to provide a chamber to receive the syringe piston and at least part of the barrel. The plunger has deflectable engagement elements at its forward end so it is pushed into the body, it reliably displaces the syringe piston/rod to discharge the syringe contents via a hollow needle, the elements ultimately being deflected outwards as the contents are fully discharged so as not to impede syringe retraction into the hollow plunger. The plunger also has latch opening projections at its forward end.

11 Claims, 3 Drawing Sheets

FOREIGN PATENT DOCUMENTS

| WO | WO 90/06146 | 6/1990 |
| WO | WO 92/18187 | 10/1992 |
| WO | WO 95/11713 | 5/1995 |
| WO | WO 96/05879 | 2/1996 |
| WO | WO 96/27403 | 9/1996 |

* cited by examiner

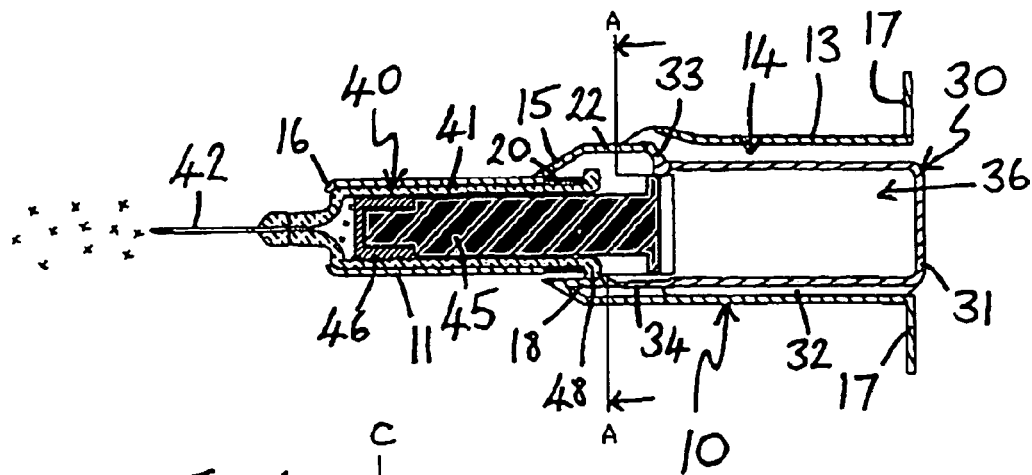
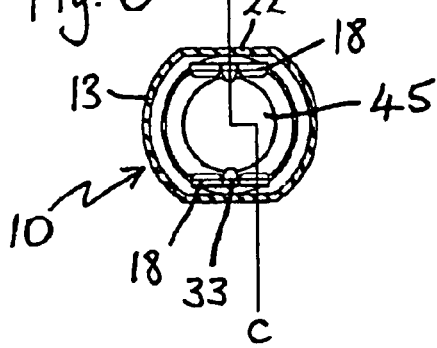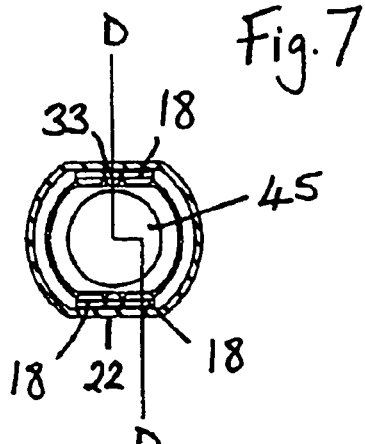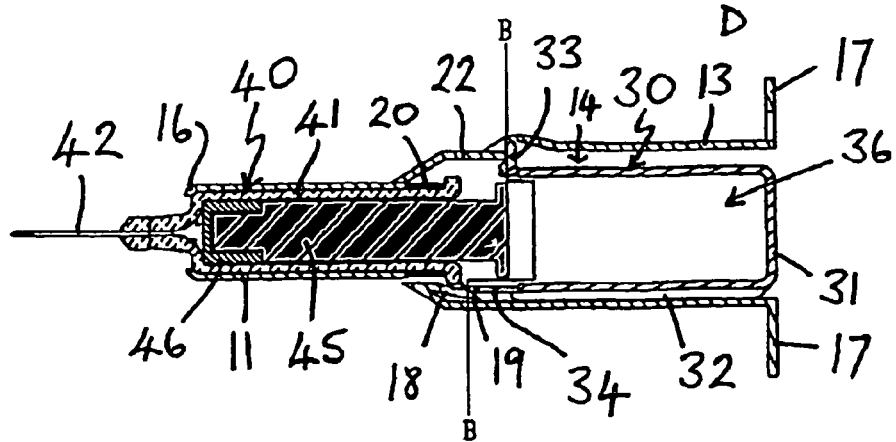

ACTUATOR AND CONTAINMENT DEVICE FOR A SYRINGE

This application is a 371 of PCT/GB2004/002921 filed on Jul. 5, 2004.

TECHNICAL FIELD

This invention concerns a device which is operable to discharge the contents of a syringe and then serve as a container for the syringe.

BACKGROUND ART

Many drug doses are supplied in miniature glass syringes (MGS), for example of the type supplied under the trade name BD HYPAK by Becton, Dickinson and Company. Each such syringe has an integral needle and it is factory filled with a specific drug dose.

There is a demand for needle point safety and the elimination of needle-stick risk in respect of such pre-filled syringes which cannot be met by regular automatic needle retraction syringes. An object of this invention is to address this demand.

Earlier known syringes and blood sampler devices, as described in the applicant's earlier WO 92/18187 and WO 93/23098 employ an integrally moulded latch array to hold a needle assembly in position against the force of a spring until the injection is completed when the latches are released by the action of a plunger formation thus allowing the needle to retract safely into the device under the released force of the spring.

SUMMARY OF THE INVENTION

According to the present invention a device is now proposed which accepts a pre-filled MGS and which permits a user to administer the dose in the normal way, but at the end of the dose delivery causes the whole MGS automatically to retract into the device, thus retracting and encapsulating the needle so that the chance of needle-stick accidents are eliminated.

More specifically, the invention provides an actuator and containment device for a syringe of the type comprising at least a barrel and piston means displaceable within the barrel to expel any contents of the barrel, usually via a hollow needle, said device comprising a hollow body, a spring and a plunger, in which respect the hollow body has internal latching formations and is adapted to house the syringe barrel and piston means with any needle projecting outside the body, the spring is disposed to act between the body and the syringe barrel, which barrel, in initial use of the device, is retained against the force of the spring by means of the latching formations, and the plunger is slidably located in the body to displace the piston means of the syringe, provides means whereby the latching formations of the body can be disengaged from the syringe barrel enabling the spring to retract the entire syringe, including any needle, into the hollow body, and also provides a chamber for reception of at least a portion of the syringe after the spring has so acted, characterised in that the plunger has deflectable edge members whereby it can abut and displace the piston rod and the hollow body has internal deflector means which serve to deflect the edge members of the plunger out of the path of retraction of the syringe barrel.

BRIEF DESCRIPTION OF THE DRAWINGS

In preferred embodiments of the device of the invention the internal latching formations of the body are integrally moulded with the body, i.e. moulded in one piece as part of the body upon production of same.

The invention also provides an assembly comprising a syringe fitted into an actuator and containment device as just defined.

The syringe in such an assembly may be provided with a hollow needle from the outset, or such a needle may be fitted just prior to use.

The syringe maybe a proprietary pre-filled MGS, as outlined above, but it could be of a different type, for example of plastics material instead of glass, and/or not supplied as pre-filled, but filed just prior to fitting into the device of the invention.

Figure 1:
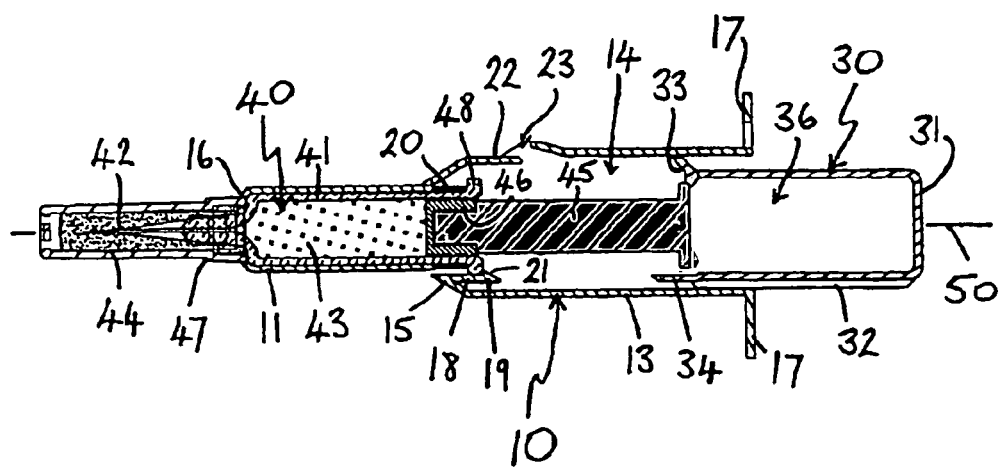
Figure 2:
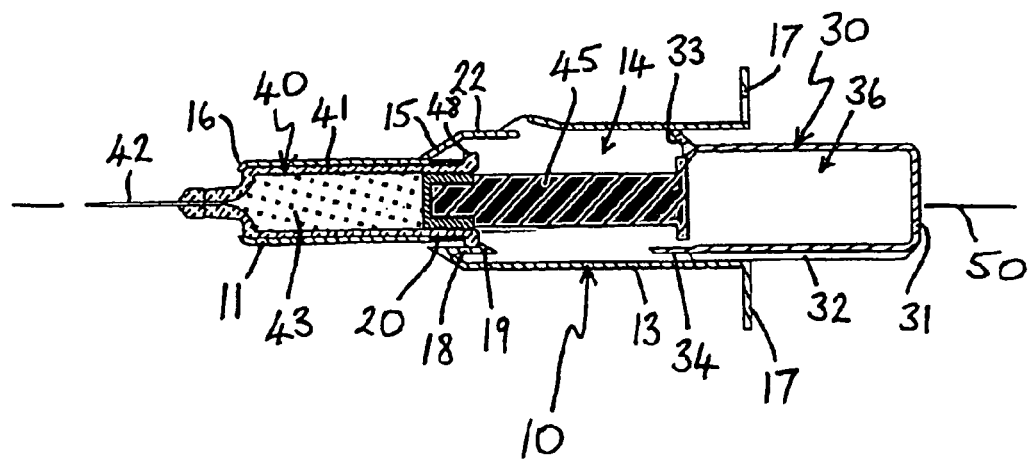
Figure 5:
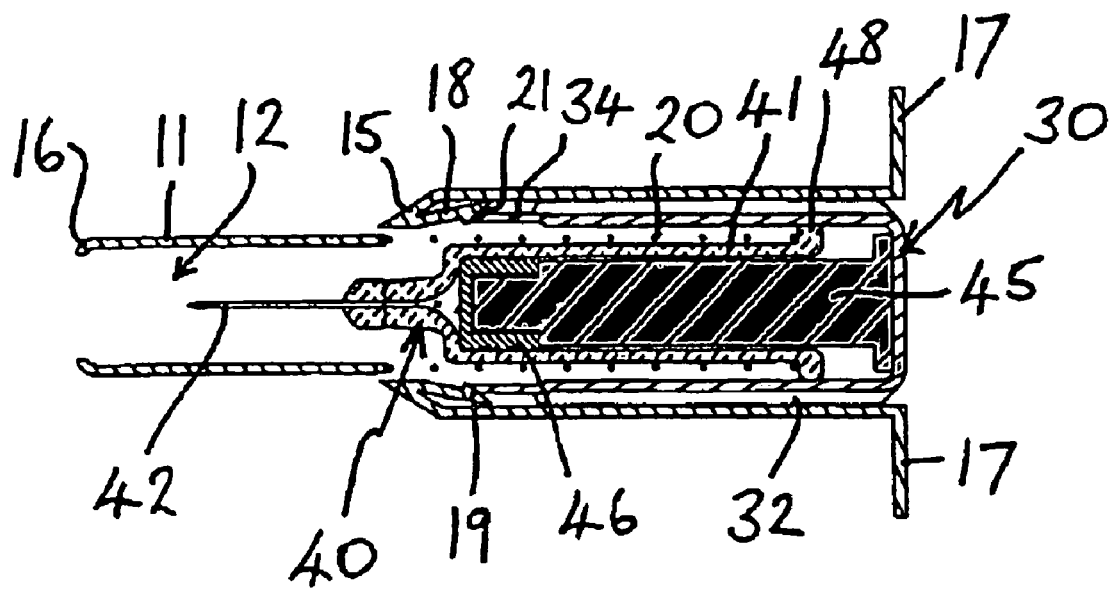

The invention will be described further, by way of example, with reference to the accompanying drawings, in which:

FIG. 1 is a longitudinal section through a preferred practical embodiment of the device of the invention assembled with a pre-filled MGS, the lower half of the figure being taken along a line offset to the upper half, so as to show the different configuration of the device at these positions, as indicated by lines C-C and D-D respectively in the transverse cross-sections of FIGS. 6 and 7;

FIGS. 2 to 4 are comparable longitudinal sections of the same assembly as in FIG. 1 showing the sequence of operation of the device through discharge of syringe contents;

FIG. 5 is a straight longitudinal cross-section of the same assembly showing the final stage of its operation, namely retraction of the entire MGS into the device;

FIG. 6 is a transverse cross-section through the assembly of FIG. 3 along line A-A therein in the direction of the arrows; and FIG. 7 is a transverse cross-section through the assembly of FIG. 4 along line B-B therein in the direction of the arrows.

Referring to the drawings, a preferred practical embodiment of the device of the invention consists of only three components, namely a hollow body 10, a spring 20 and a plunger 30. In addition, a miniature glass syringe (MGS) 40 is fitted into the device to provide an assembly of the invention.

The hollow body 10 of the device is of generally cylindrical form and its longitudinal axis is indicated at 50. It comprises a front end portion 11 which is cylindrical, i.e. of circular cross-section, and defines a forward chamber 12 (see FIG. 5) and a rear end portion 13, which in cross-section approximates to an elliptical shape having flattened regions at opposing sides, as is shown in FIGS. 6 and 7. The rear end portion 13 defines a main chamber 14 of the device which is of larger diameter than the forward chamber 12 and is connected thereto by a tapered region 15.

The front end portion 11 has an inturned lip 16 at its front end in order to retain the syringe 40 in the hollow body 10, as will be explained later. The rear end portion 13 has opposed outwardly directed, substantially perpendicular, flanges 17 at its rear end to enable a user to grasp the device and depress the plunger 30 using only one hand.

Inside the main chamber 14, at its front end adjacent the forward chamber 12, the body 10 has a number of latching formations 18 which lie radially outwardly of the forward chamber 12. There are four such latches 18 in the illustrated embodiment. These are symmetrically arranged in the interior of the body 10 as two opposing pairs, as shown in FIGS. 6 and 7. These latching formations 18 extend generally parallel with the longitudinal axis 50 of the body 10 and at their free rear ends they have inwardly directed catch means 19 in the form of wedges, which also provide, in each case, a sloping surface 21 for co-operation with the plunger 30. The latching formations 18 are sufficiently resilient to be capable of being deflected outwards.

Also inside the main chamber 14, at its front end adjacent the forward chamber 12, and also symmetrically arranged, are a number of rearwardly directed formations 22, which serve as deflector means for parts of the plunger 30, as will be explained. There are two such formations 22 in the illustrated embodiment, rather like projecting shelves, and these are located, in each case, adjacent a pair of latches 18, as shown in FIGS. 6 and 7.

The hollow body is moulded in one piece, which means that all the above described parts and regions thereof are integrally moulded therewith. Adjacent the deflector formations 22 there are openings 23 and also slight bulges in the contour of the body 10. The interior of the main chamber 14 is formed with a series of longitudinal grooves, although these are not apparent in the drawings.

The spring 20 is a helical spring which seats within the forward end of the main chamber 14 of the hollow body 10. It is of substantially the same external diameter as the front end portion 11, as shown in FIGS. 1 to 5.

The plunger 30 is also of hollow form, but has a closed end 31. It defines a chamber 36. It is of a cross-sectional shape corresponding to that of the rear end portion 13 of the hollow body 10, but somewhat smaller so that it is able to fit slidingly within the main chamber 14 of the body 10.

At its forward end, remote from its closed end 31, the plunger 30 has symmetrically arranged deflectable edge members 33 located between respective pairs of symmetrically arranged latch opening formations 34. The latter have surface portions adapted for co-operating with the sloping surfaces 21 of the catch means 19 so as to outwardly deflect the latching formations 18 of the hollow body 10. Thus the arrangement of the latch opening formations 34 peripherally of the plunger 30 corresponds to the arrangement of the latching formations 18 in the hollow body 10.

Externally, the plunger has a series of longitudinal ribs 32 which, in use, co-operate with, i.e. fit into, the longitudinal grooves inside the main chamber 14 to guide the plunger 30 and maintain its alignment relative to the body 10 as the plunger 30 is pushed into the main chamber 14. In other words, the plunger 30 is prevented by interengagement of the ribs 32 and grooves from rotating inside the chamber 14. This is important in ensuring that the aforesaid formations 34, 18 are correctly aligned to bring about release and retraction of the syringe 40 in use of the device.

The device thus far described serves as both an actuator for the syringe 40 and a container for the syringe 40 once its contents have been discharged.

The syringe 40 is an MGS of a well known, commercially available type comprising a barrel 41, which is pre-filled with a measured dose 43 of fluid for injection and sealed off by a rubber piston 46, a hollow needle 42 extending from the barrel 41 and covered by a sheath 44, and a piston rod 45. The piston rod 45 fits to the piston 46 thus providing piston means which is displaceable into the barrel 41 to discharge the dose 43 via the needle 42, once the sheath 44 is removed therefrom.

Sometimes, within the technical field, a pre-filled syringe barrel sealed off by a piston, as just described, but without a piston rod, and optionally without a needle is referred to as "a cartridge". However, the term "cartridge" is also used, by some, to refer to an entire MGS, inclusive of needle and piston rod. To avoid such confusion, the term "cartridge" will not be used herein. Only the individual terms, designated above will be used, and the term syringe 40 is to be understood as meaning the entire combination of the barrel 41, the needle 42 and the piston means 45, 46.

In use, the syringe 40 is located in the device as shown in FIG. 1. Assembly of the syringe/device combination may suitably be achieved by starting with the hollow body 10 and inserting a tubular guidance tool through the open front end of the front end portion 11 and a considerable distance through the body into the main chamber 14. The spring 20 is then dropped into the open rear end of the main chamber to encircle said tubular tool. The syringe 40, fitted with its removable sheath 44, is then inserted from the rear end of the main chamber 14. The sheath 44 fits inside the tubular tool up to a shoulder 47 near the base of the sheath, which abuts the tool rim. A further tool can then be inserted from the rear end of the main chamber 14 to exert pressure as the first mentioned guidance tool is withdrawn. This further tool pushes the barrel 41 down so that an outward flange 48 at the rear end of the barrel 41 compresses the spring 20 and then deflects the latching formations 18 so as to seat behind the catch means 19 as the latching formations 18 return back home behind.

The plunger 30 is then inserted partially into the rear end of the main chamber 14 of the body 10, to the position shown in FIG. 1, with the deflectable edge members 33 making contact with the end of the piston rod 45 of the syringe 40.

The operation of the assembly of the device 10, 20, 30 and the syringe 40 is readily understood by reference to FIGS. 1 to 5, which show the sequence of steps involved.

Firstly, with reference to FIGS. 1 and 2, to enable injection of the syringe contents 43 into a patient or user, the sheath 44 is removed and the needle 42 is inserted into the patient. Then, as shown in FIG. 3, the plunger 30 is pushed inwardly of the hollow body main chamber 14. The deflectable edge members 33 at the forward (inner) end of the plunger 30 thus push in the piston rod 45 and piston 46 to discharge the contents 43 of the syringe barrel 41 via the needle 42. The syringe barrel 41 all the while is held in position in the hollow body 10 by means of the latches 18 and against the force of the spring 20.

When the dose 43 discharge is almost completed, pressure on the plunger end 31 forces the edge members 33 against the deflector formations 22. This causes those members 33 to be deflected radially outwardly of the plunger 30 to lie in the hollow body 10, as is apparent in FIG. 4. Simultaneously, the latch opening formations 34, also projecting at the forward end of the plunger 30, contact the sloping surfaces 21 of the wedge shaped catch means 19, and force the latches 18 to deflect outwards. This releases the flange 48 and allows the spring 20 to act thereagainst so as to immediately retract the entire syringe 40 into the hollow body 10, as shown in FIG. 5. In this respect, the chamber 36 of the fully inserted plunger 30 is positioned to receive the piston rod 45 and much of the spent syringe barrel 41, while the front end of the barrel 41 and the needle 42 lie in the forward chamber 12 of the hollow body 10, but still a considerable distance in from the terminal lip 16. Moreover, the aperture defined by the lip 16 is sufficiently small as to prevent a human finger gaining access. Thus, immediately upon discharge of the syringe 40, the needle 42 is automatically retracted and encapsulated so that there can be no possibility of needle-stick injury occurring.

The foregoing is illustrative not limitative of the scope of the invention. Many variations in detail of the construction of the device compared to the illustrated embodiment are possible, particularly as regards the number, arrangement and actual configuration of the deflectable latch formations and the latch opening formations and the deflectable or frangible edge members. Moreover, although it is preferred that the hollow body is moulded in one piece and that the device consists of only three components these are not essential attributes of the invention. Also, as has already been pointed out, the form and type of syringe used with the device in an assembly of the invention may vary from the preferred forms of MGS which have been described and illustrated. Syringes of plastics, syringes with needles fitted only just prior to use, and after assembly in the device, and syringes having other forms of piston means to those described are all within the scope of the invention.

The invention claimed is:

1. An actuator and containment device for a syringe of the type comprising at least a barrel and piston means displaceable within the barrel to expel any contents of the barrel, usually via a hollow needle, said device comprising a hollow body, a spring and a plunger, in which respect the hollow body has internal latching formations and is adapted to house the syringe barrel and piston means with any needle projecting outside the body, the spring is disposed to act between the body and the syringe barrel, which barrel, in initial use of the device, is retained against the force of the spring by means of the latching formations, and the plunger is slidably located in the body to displace the piston means of the syringe, said plunger also having, at its forward end in direction of its insertion into the body, latch opening formations operative to disengage the latching formations of the body from the syringe barrel enabling the spring to retract the entire syringe, including any needle, into the hollow body, and said plunger also providing a chamber for reception of at least a portion of the syringe after the spring has so acted, wherein said plunger also has at its forward end in direction of its insertion into the body, and separate from said latch opening formations, deflectable edge members whereby it can abut and displace the piston rod and said hollow body has, separate from said latching formations which retain the syringe barrel, an internal deflector means which serves to deflect said deflectable edge members of said plunger out of the path of retraction of the syringe barrel.

2. A device according to claim 1 wherein the hollow body is generally of cylindrical form and has a longitudinal axis and also defines a main chamber in which the plunger is slidably located and a forward chamber which is of smaller cross-section than the main chamber and extends from the main chamber beyond the end of plunger movement to house the syringe barrel in initial use of the device.

3. A device according to claim 2 wherein the latching formations of the body are provided in the main chamber of the body adjacent to the forward chamber but lying radially outwardly with respect to the forward chamber.

4. A device according to claim 1 wherein the latching formations extend generally parallel with the longitudinal axis of the hollow body to free ends which have radially inwardly directed catch means for retaining the syringe barrel against the force of the spring, the latching formations also being deflectable radially outwardly to enable capture of the syringe barrel by said catch means and its later release therefrom.

5. A device according to claim 1 wherein the plunger and the latching formations have co-operating surface portions whereby the plunger can effect radially outward deflection of the latching formations to release the syringe barrel from the catch means.

6. A device according to claim 1 wherein the hollow body is moulded in one piece and the latching formations are integrally moulded therewith.

7. A device according to claim 1 wherein the latching formations are symmetrically arranged in the interior of the hollow body.

8. A device according to claim 1 wherein the deflectable edge members are symmetrically arranged at the forward edge of the plunger.

9. A device according to claim 1 consisting of only a hollow body, a spring and a plunger.

10. An assembly comprising a syringe and an actuator and containment device for said syringe as claimed in any preceding claim, said syringe comprising a barrel, a hollow needle, and piston means displaceable within the barrel to expel contents of the barrel via said needle, wherein the hollow body of the device houses the syringe barrel and piston means with the needle initially projecting outside the body and the spring is disposed inside the body and acts between the body of the device and the barrel of the syringe.

11. An assembly comprising a syringe and an actuator and containment device for said syringe as claimed in claim 1, said syringe comprising at least a barrel and piston means displaceable within the barrel to expel contents of the barrel, usually via a needle, wherein the hollow body of the device houses the syringe barrel and piston means and the spring is disposed inside the body and acts between the body of the device and the barrel of the syringe.

* * * * *